United States Patent [19]

Shuman et al.

[11] Patent Number: 5,594,654

[45] Date of Patent: Jan. 14, 1997

[54] BENEFICIAL INSECT COUNTING AND PACKAGING DEVICE

[75] Inventors: Dennis Shuman, Gainesville; Carl A. Litzkow, Newberry, both of Fla.; Sergey Kruss, Norwood, Mass.; James A. Coffelt, Bakersfield, Calif.; Frederick L. Petitt; David O. Wietlisbach, both of Orlando, Fla.

[73] Assignee: The United States of America as represented by the Secretary of Agriculture, Washington, D.C.

[21] Appl. No.: 390,833

[22] Filed: Feb. 17, 1995

[51] Int. Cl.$^6$ .................................................. G06F 17/00
[52] U.S. Cl. .................................... 364/478.01; 364/555
[58] Field of Search ................................... 364/478, 555; 340/573; 250/338.1, 339.02

[56]                References Cited

U.S. PATENT DOCUMENTS

| | | | |
|---|---|---|---|
| 4,410,967 | 10/1983 | Hendricks | 367/87 |
| 4,809,554 | 3/1989 | Shade et al. | 73/587 |
| 4,937,555 | 6/1990 | Litzkow et al. | 340/540 |
| 5,005,416 | 4/1991 | Vick et al. | 73/587 |
| 5,473,942 | 12/1995 | Vick et al. | 73/587 |

OTHER PUBLICATIONS

Shuman et al., "An Electronic Fall–Through Probe Insect Counter Computer System for Monitoring Infestation in Stored Product Facilities", ASAE Meeting Presentation Paper No. 946501, Atlanta, Georgia (Dec. 13–16, 1994), pp. 1–12.

Hook et al., "Digital I/O with the PC", Dr. Dobbs Journal, Apr. 1994, pp. 64–70.

White et al., Journal of the Kansas Entomological Society 63(4):506–525 (1990).

Reed et al., Journal Econ. Entomol. 84(4):1381–1387 (1991).

Hagstrum et al., Proceedings 6th International Working Conference on Stored–Product Protection, Canberra, Australia, 1994, in press.

Bauwin et al., In: Storage of Cereal Grains and Their Products; 2nd Ed., ed. C. M. Christensen, 115–157, 1974; St. Paul, MN: American Association of Cereal Chemists.

Noyes et al., In: Management of Grain, Bulk Commodities, and Bagged Products, Circular E–912, 71–79, Cooperative Extension Service, Oklahoma State University, 1991.

Hagstrum et al., In: Management of Grain, Bulk Commodities, and Bagged Products, Circular E–912, 65–69, Cooperative Extension Service, Oklahoma State University, 1991.

D. E. Hendricks, Environmental Entomology 14(3):199–204 (1985).

D. E. Hendricks, J. Econ. Entomol. 82(2):675–684 (1989).

Greenhouse Product News, pp. 23–24, Jan. 1995.

Agricultural Research Magazine, p. 31, Oct. 1994.

Florida Entomol. Soc., Aug. 1994. Poster presentation and press release by Sean Adams.

Subramanyam et al., J. Econ. Entomol. 83(3):1102–1109 (Jun. 1990).

Subramanyam et al., J. Econ. Entomol. 82(6):1817–1824 (Dec. 1989).

Barak et al., Journal of the Kansas Entomological Society 63(4):466–485 (1990).

(List continued on next page.)

*Primary Examiner*—Paul P. Gordon
*Attorney, Agent, or Firm*—M. Howard Silverstein; John Fado; Gail E. Poulos

[57]                 ABSTRACT

An automated system has been developed to count and package beneficial insect larvae or eggs and includes a funnel-shaped container which sits in the top portion of a sensor head and a turntable with multiple containers located below the sensor head, for collecting larvae or eggs as they drop through the sensor head. The system accurately records the number and time stamps each insect larva or egg detection as they drop through a sensor head.

7 Claims, 10 Drawing Sheets

OTHER PUBLICATIONS

Cuperus et al., Journal of the Kansas Entomological Society 63(4):486–489 (1990).

Wei et al., 6th International Working Conference on Stored Product Protection, Canberra, Australia (Apr. 1994).

Shuman et al., Presentation at Annual International Research Conference on Methyl Bromide Alternatives and Emissions Reductions (Nov. 1994) ["Automated Monitoring of Stored–Grain Insects: Acoustical and Electronic Grain Probe Methods"].

Dennis Shuman, Hand–out at ARS/FGIS Working, with Non–Gov't People Present (Oct. 25, 1991) ["Electronic Detection of Insects in Grains"].

Subramanyam et al., J. Agric. Entomol 6(1):9–21 (Jan. 1989).

Trece Incorporated, Storgard WB Probe II Insect Monitoring System, 1 page.

AgriSense–BCS Ltd., Trappit Insect Probe Trap, Technical Information, 1 page.

BENEFICIAL INSECT COUNTING AND PACKAGING DEVICE

BACKGROUND OF THE INVENTION

1. Field of the Invention

The invention relates to an apparatus and a process for counting and packaging beneficial insects larvae or eggs.

2. Description of the Prior Art

Protection of agricultural commodities from insect infestations and the direct loss caused by insects are costly. Chemical insecticides are used to control insects that damage agricultural commodities such as grapes, cotton, barley, citrus, pecans, Christmas trees, ornamental plants, etc. However, recent concerns about insecticide residues on commodities, resistance of insects to chemical insecticides, hazardous exposure to pesticide applicators, environmental contamination, destruction of natural biocontrol agents, such as beneficial insects, and lack of newly developed insecticides have increased the need for alternative control methods. Furthermore, as pests become more resistant to pesticides, more frequent treatments are required which increases the human health hazard.

Control methods, such as those that use beneficial insects, lessen the need for chemical insecticides. However, the standard methods for rearing beneficial insects are labor intensive. There are a few methods for collecting and delivering known quantities of beneficial insects to infested plants or stored grain products which use weight and/or volume as a measure of number of insects. There remains a need in the art for automated counting and packaging of beneficial insect larvae and eggs. The present invention provides such an automated system which solves some of the problems associated with prior art methods of manual counting and packaging and methods using weight and/or volume measures.

SUMMARY OF THE INVENTION

It is therefore an object of the present invention to provide an automated insect counting and packaging system for rearing beneficial insects.

Another object of the present invention is to provide a system that includes a means for counting insects that includes a sensor head.

A still further object of the present invention is to provide a system that includes a means for detecting insects passing through a sensor head and a means for analyzing signals produced by a means for detecting insects passing through a sensor head.

A further object of the invention is to provide a method for counting and packaging beneficial insects that includes a counting means for collecting and counting insect larvae and eggs.

Another object of the present invention is to provide a method for counting and packaging beneficial insects that includes collecting and counting insect larvae or eggs with a counting means for collecting and counting insect larvae and eggs, detecting the passage of insect larvae or eggs through a counting means using a means for detecting insect larvae or eggs passing through the counting means, collecting and containing insect larvae or eggs with a means for collecting and containing the insect larvae and eggs that includes a turntable with a plurality of container means, and receiving and analyzing signals from the detecting means in order to turn the turntable when there is a predetermined maximum number of larvae or eggs in each of said plurality of container means.

Further objects and advantages of the invention will become apparent from the following description.

DETAILED DESCRIPTION OF THE INVENTION

The present invention, a beneficial insect counting and packaging (BICAP) system 50 for rearing beneficial insects, is useful for collecting and delivering known quantities of beneficial insect larvae and eggs. The system is used for counting and packaging insect eggs or larvae, especially, for example, those used for biological control purposes and is related to pending U.S. patent application Ser. No. 08/390,834, filed Feb. 17, 1995 an Electronic Grain Probe Insect Counter.

Figure 1:
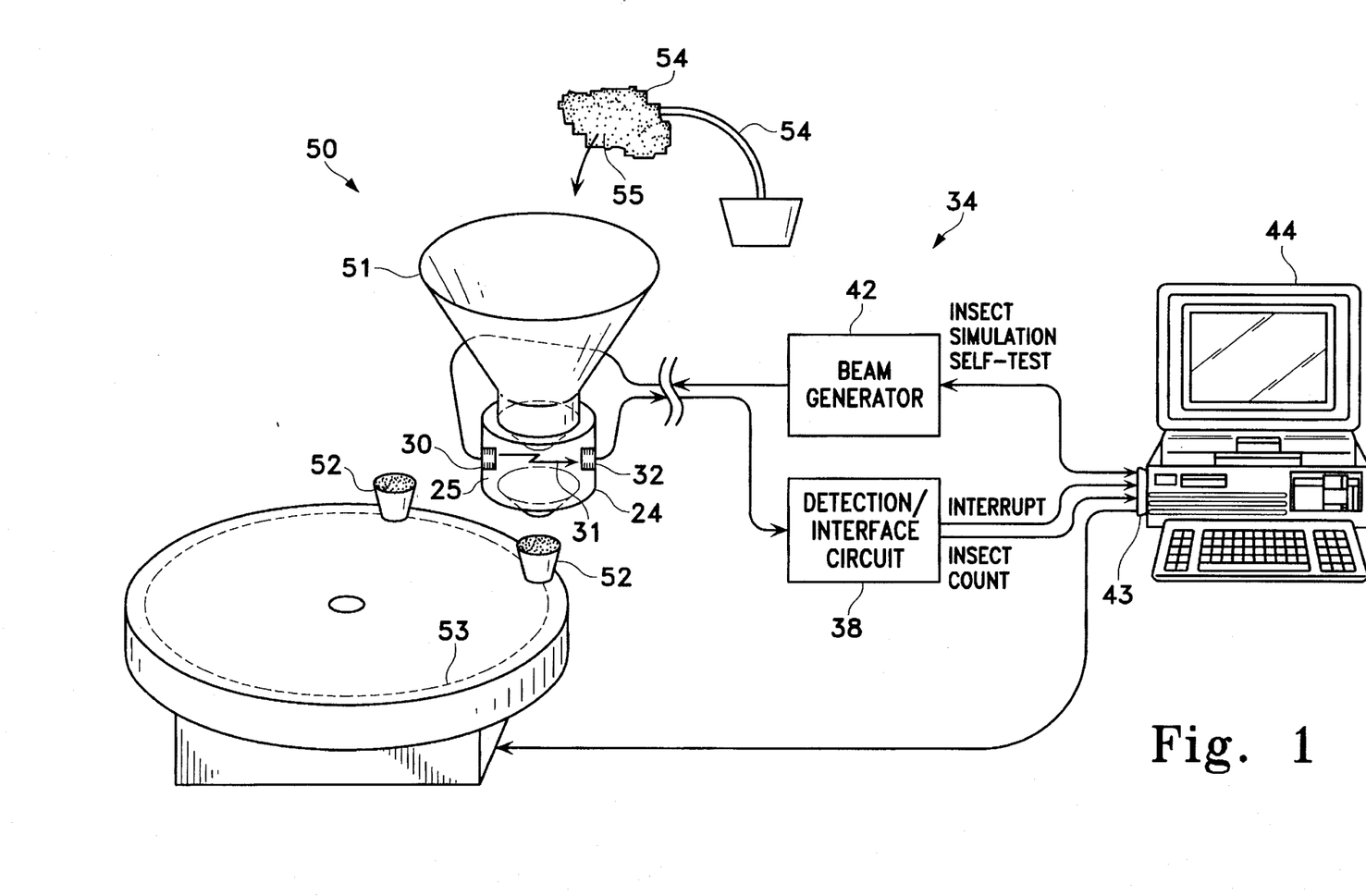
FIG. 1 shows Beneficial Insect Counting and Packaging (BICAP) system 50.
Figure 5:
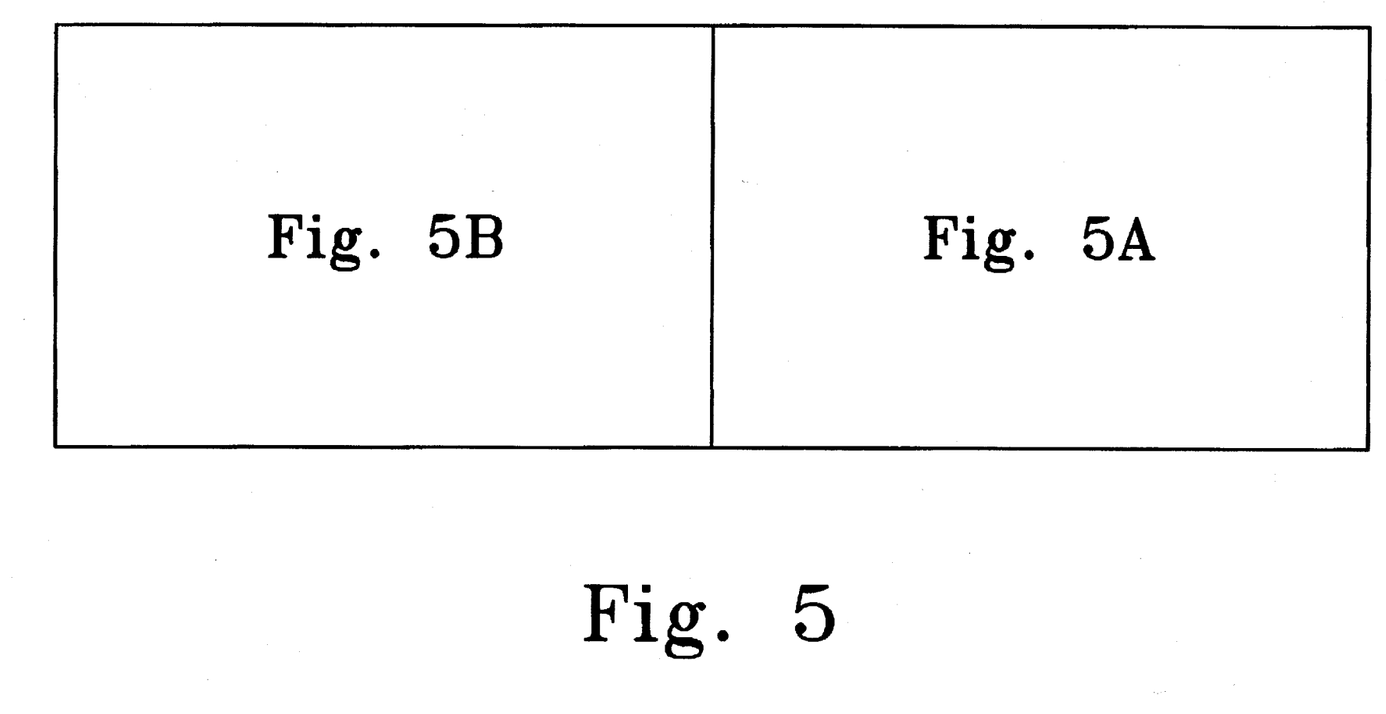
FIG. 5 is a diagram of the system circuitry 34.
Figure 5A:
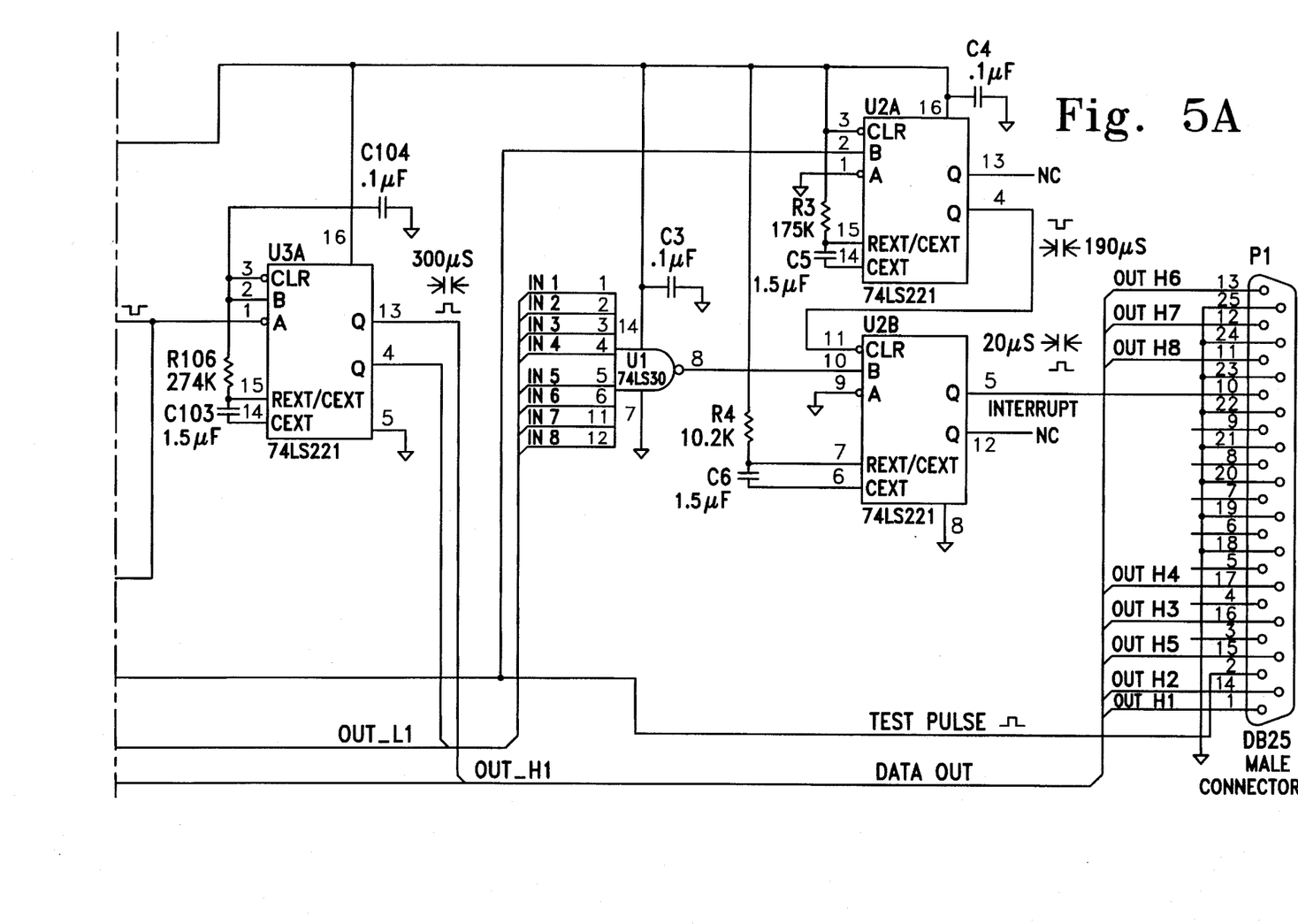
Figure 5B:
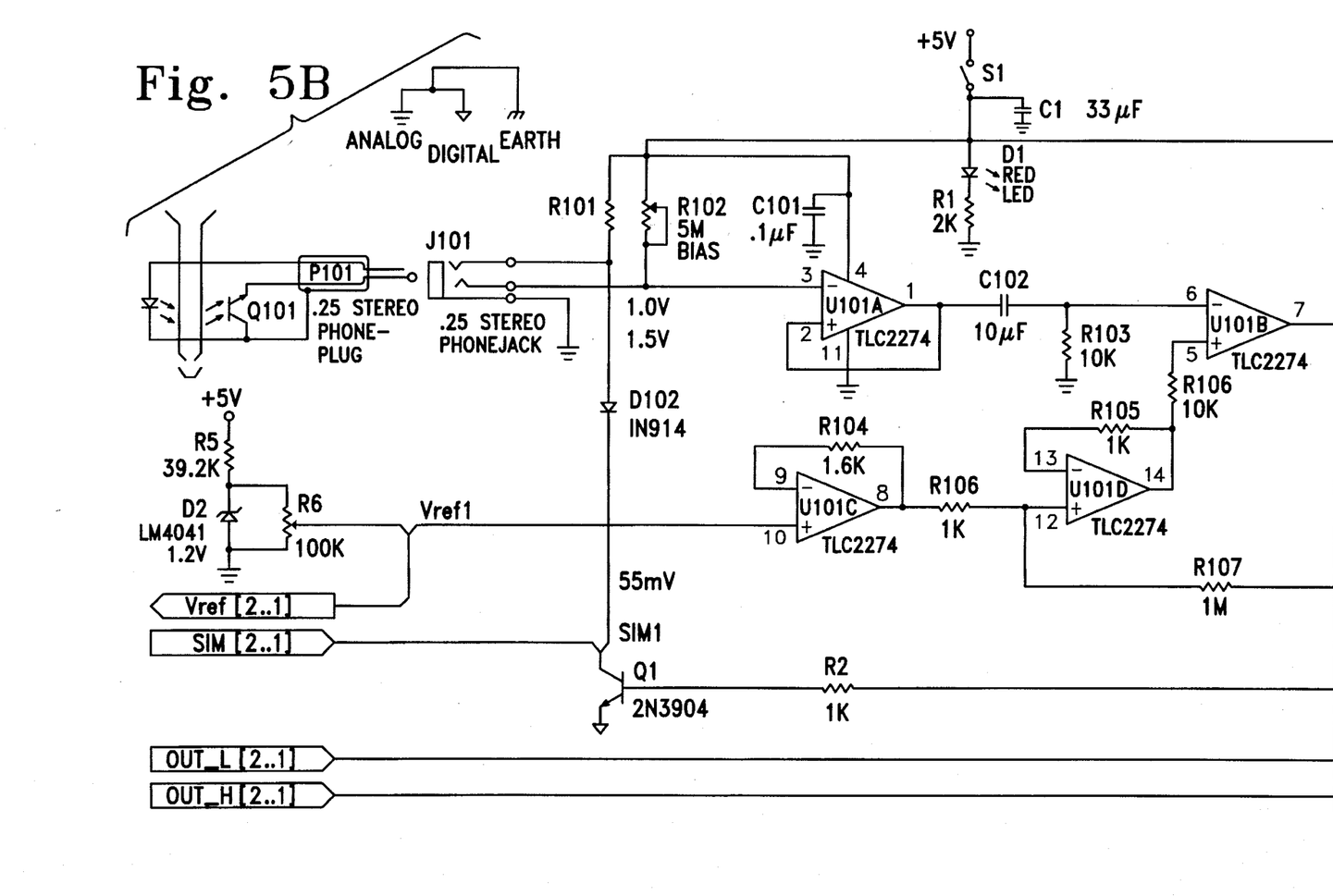

BICAP 50 (FIG. 1) counts larvae or eggs of insects as they drop from plants or a container and has a funnel-shaped container 51 which may be, for example, constructed of glass or plastic, attached to inner top section 27 of a sensor head 24. The insect larvae or eggs drop through container 51 and sensor head 24 into a collection cup 52 mounted on turntable 53. Turntable 53 can be any variety of available turntables such as one which rotates a slide projector carousel, a turntable for a fraction collector, etc. Sensor head 24 output is connected to a computer 44 through system circuitry 34 (see FIG. 5). When cup 52 receives a selected number of insect larvae or eggs, computer 44 rotates turntable 53 in order to begin filling the next cup. Computer 44 can be connected to up to seven turntables through the computer's parallel port and up to 47 turntables per digital I/O board having 96 input/output pins (FIG. 1). The analysis of the information received from sensor head 24 is performed on (a) a computer with one input line and one output line from it's parallel port for interfacing with one sensor head 24 and one turntable 53, respectively, or (b) a computer with a commercial digital I/O computer board for applications requiring more than 7 turntables.

Figure 2:
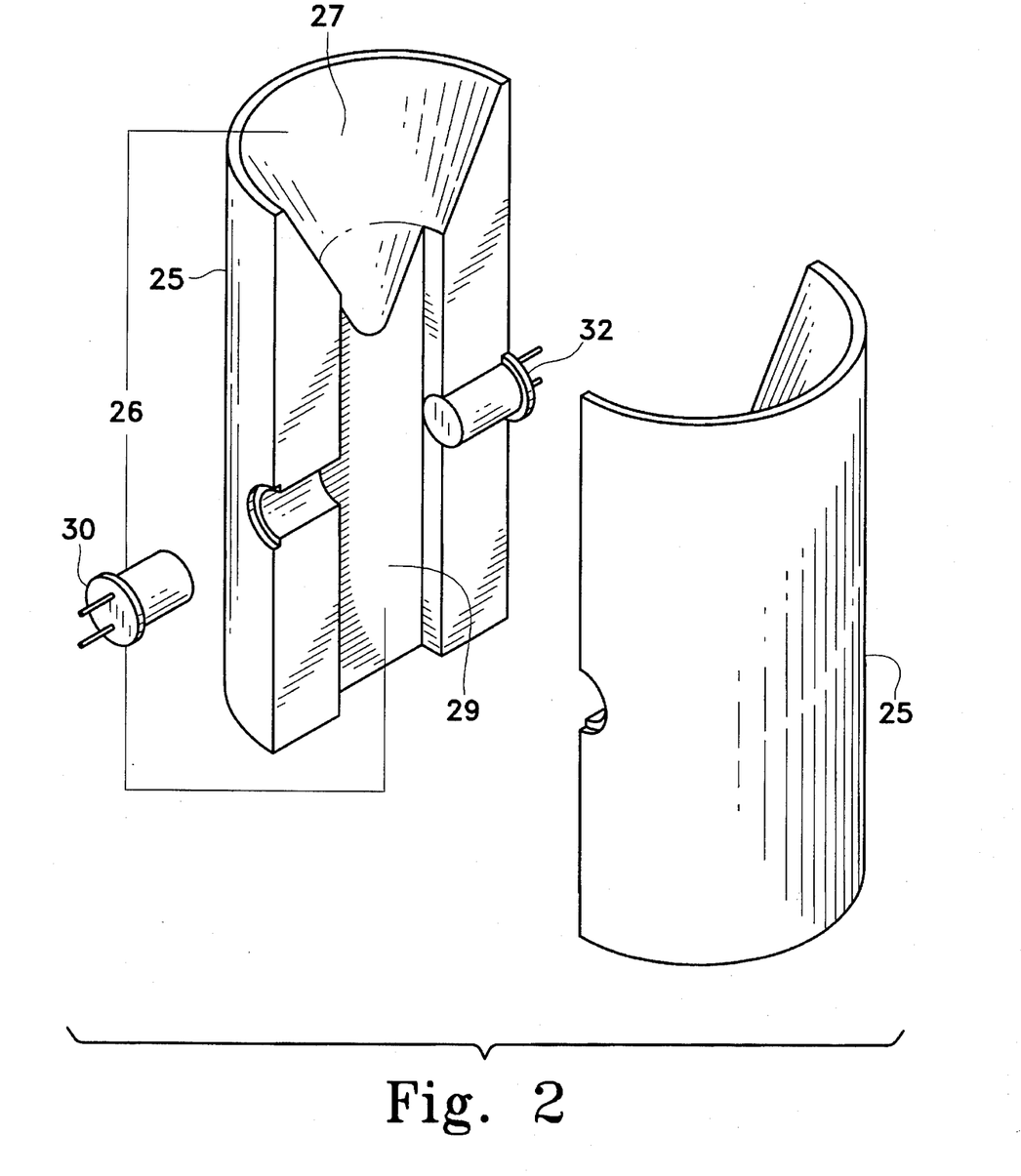
FIG. 2 is a split view of one embodiment of sensor head 24 and its internal design.

As illustrated in FIG. 1, sensor head 24 detects the passage of insect larvae or eggs from funnel-shaped container 51 to collection cup 52. Sensor head 24 includes a wall portion 25 defining therein an interior chamber 26 (not shown). Sensor head 24 is fabricated by molding resin and/or by machining PVC stock and may be of any suitable, reasonably strong and durable material including, for example, various metals such as brass or steel, or any of the plastics, acrylics, or polycarbonates such as LEXAN™, Plexiglass, etc., or thermosetting plastic composites used for injection molding. The inner top section 27 of chamber 26 is funnel-shaped and the lower part is a longitudinally centered inner channel 29 which is approximately 1.8"= 0.505"×0.175" (FIG. 2). Located midway on one side of channel 29 is an infrared light-emitting diode (LED) 30 which produces a beam 31 that is sensed by an infrared phototransistor 32 located opposite of LED 31. For the entire system infrared LEDs' beam 31 strengths in all sensor heads are set by a single adjustment and then the quiescent operating point of each phototransistor 32 is adjusted to optimize performance for the range of insect sizes of interest and to compensate for structural and LED tolerances. Phototransistor 32 is operated with reversed collector and emitter connections to reduce its gain and thus keep the phototransistor 32 in it's linear region so that it's output signal is proportional to the size of the insect passing through beam 31.

Figure 3:
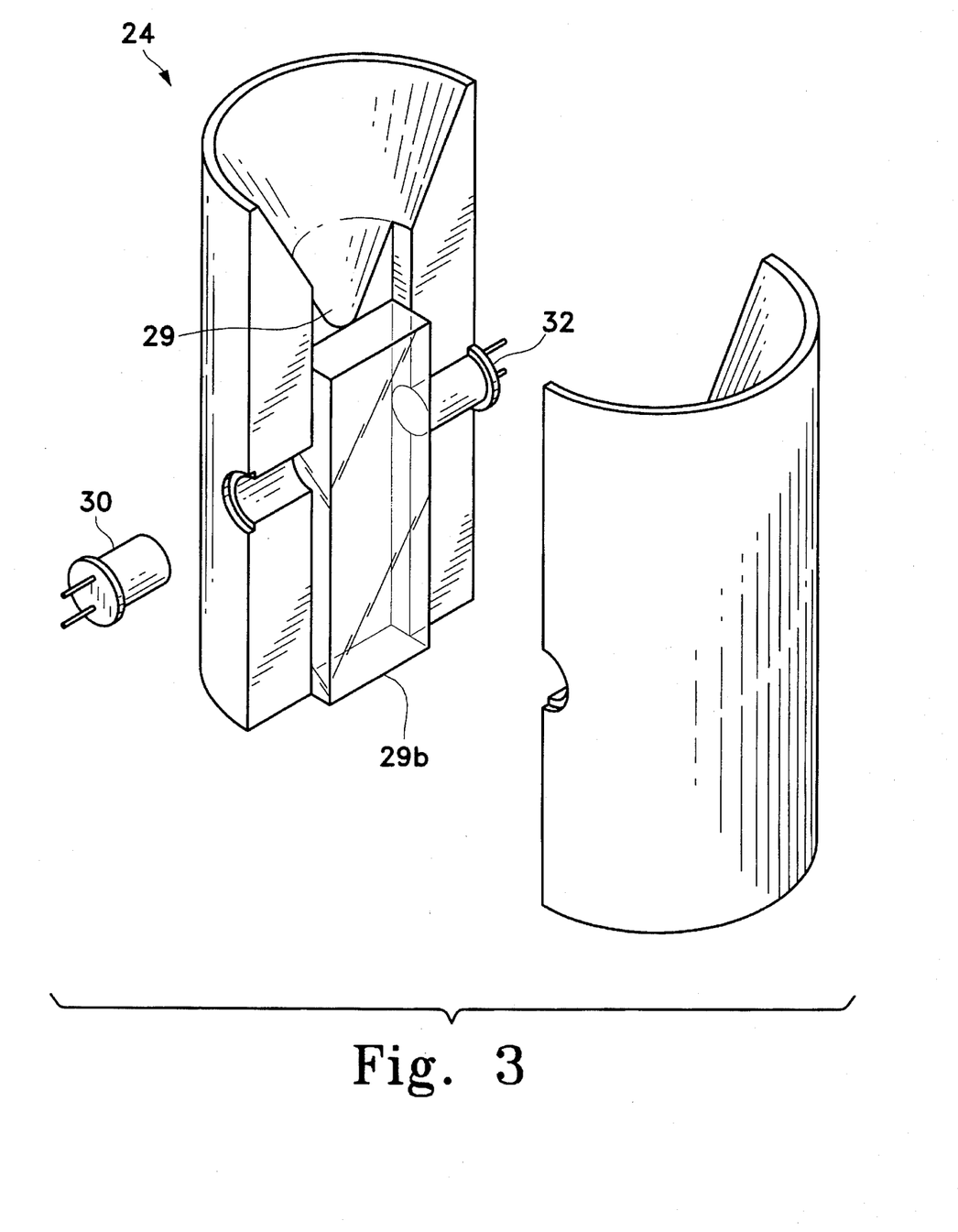
FIG. 3 is a split view of sensor head 24 with transparent insert.

Inner top section 27 and channel 29 are coated with a non-stick material, such as TEFLON™ (i.e. polyetrafluorethylene) and fluorinated ethylenepropylene resins, to minimize the possibility of larvae sticking or loitering in the vicinity of beam 31. Initial tests revealed that some insect species could grab onto the edges where sensor element 30 and 32 ends are flush against channel 29 and this causes counting errors. This is corrected by using a transparent acetate insert 29b in channel 29 (see FIG. 3). The insert and channel 29, in which it is positioned, are slightly tapered downward so that insert 29b does not slide out of the bottom of channel 29.

Figure 4A:
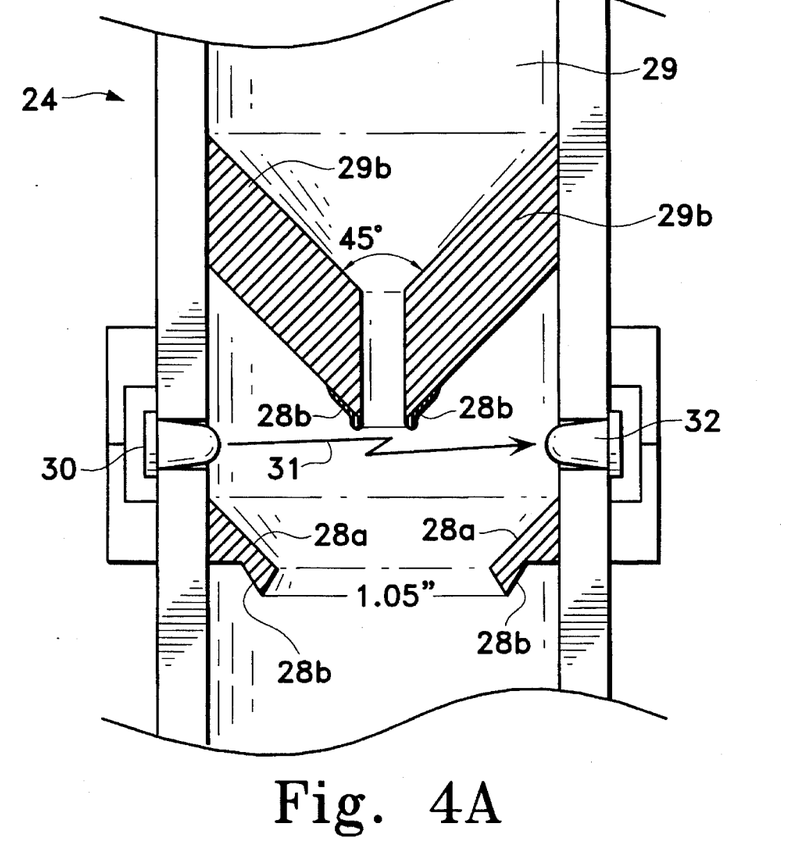
FIG. 4A is a cross-section of sensor head 24 showing funnel-shaped insert 28 and bottom ring 28a, both with downward projecting lips 28b.
Figure 4B:
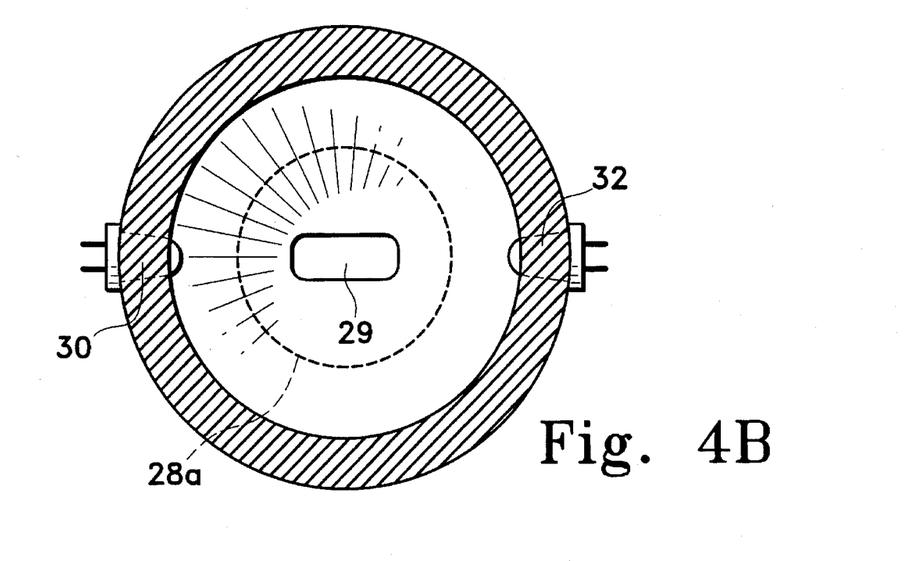
FIG. 4B is a cross-section of sensor head 24 showing bottom ring 28a and channel 29.

Another embodiment of the sensor head channel 29 is shown in FIG. 4a and 4b. Transparent insert 29b in channel 29, above, can get covered with dust over time which degrades insect counting performance. To overcome the problem of dust degrading counting performance, channel 29 has sensor elements 30 and 32 recessed from the path of dropping insects and dust (FIG. 4a and 4b). In addition a 45° angled funnel-shaped insert 28 with downwardly projecting lip 28b is located just above phototransistor 32 and LED 30 and bottom ring 28a with downward projecting lip 28b is located just below phototransistor 32 and LED 30. Insert 28 directs insects through beam 31 and both bottom ring 28a and funnel-shaped insert 28 prevent insects from crawling from the bottom or top of the head to the sensor elements 30 and 32. Regard for surface smoothness, elimination of footholds, a Teflon coating applied on inner channel 29, inner top section 27, and funnel-shaped insert 28 with downwardly projecting lips and a bottom ring 28a in sensor head 24 minimize the possibility of larvae loitering in the vicinity of beam 31.

Figure 8:
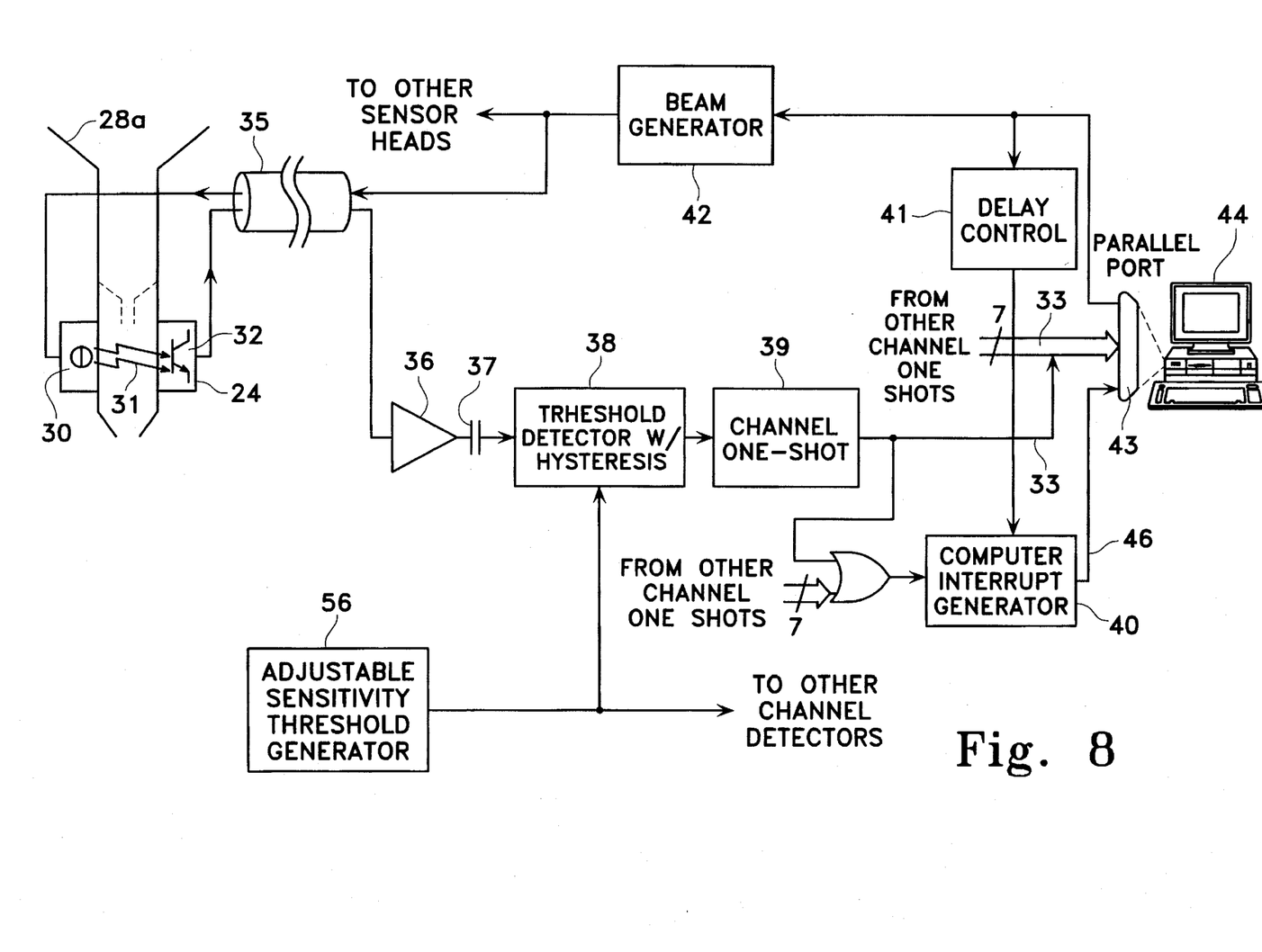
FIG. 8 is a block diagram of one sensor head channel and its functional components for parallel-input implementation.

The detecting means, an infrared beam generation/detection and computer interface circuitry (shown in FIGS. 1, 5, and 8), is responsible for generating (a) an appropriate signal to notify a computer 44 when any sensor head output change is detected and (b) another signal sent to line 33 dedicated to each individual sensor head 24 so that computer 44 can then determine through which sensor head 24 larvae or eggs dropped. Circuitry 34 includes shielded cable 35; a detecting means including buffer 36, AC coupling 37, threshold detector with hysteresis 38, a beam generator 42 and an adjustable sensitivity threshold generator 56; and an interfacing means that includes channel one-shot 39, delay control 41, and computer interrupt generator 40. The output of each phototransistor 32 is buffered and AC coupled (FIG. 5 and 8) to allow its threshold detector 38 to respond to phototransistor's 32 small signal transients created by falling larvae or eggs slightly masking beam 31. Circuitry 34 employs hysteresis (FIG. 5 and 8) for noise immunity during signal threshold crossings. A common adjustable threshold level permits setting the sensitivity to limit the minimum detectable larva or egg size, which also helps reduce particle errors. Larva- or egg-produced detector output triggers its one-shot 39 to generate a standardized 300 μs channel pulse that is applied to a digital input line on computer 44 printer parallel port 45 or on an installed digital I/O computer board (not shown) and to a common interrupt generator 40. The triggered interrupt generator 40 applies a 20 μs pulse to computer 44's interrupt line 46. This alerts the computer to scan all the channels' digital input lines 33 (within 300 μs of the detector output) to ascertain and record which sensor head had the falling larva or egg.

At scheduled times (explained below), computer 44 initiates a check of the entire system's operability by simulating a falling larva or egg via a momentary reduction of beam generator 42's output applied to all sensor heads. The first channel to respond initiates an interrupt causing all the channels' digital input lines 33 to be checked for proper response. However, since the time delay from the reaction of beam generator 42's output to a channel's pulse response is about 4 μs per meter of sensor cable, during a system self-check an interrupt delay of 190 μs is enabled to ensure receiving responses from sensor heads with the longest sensor cables before computer 44 checks the channels' digital input lines 33.

Figure 6:
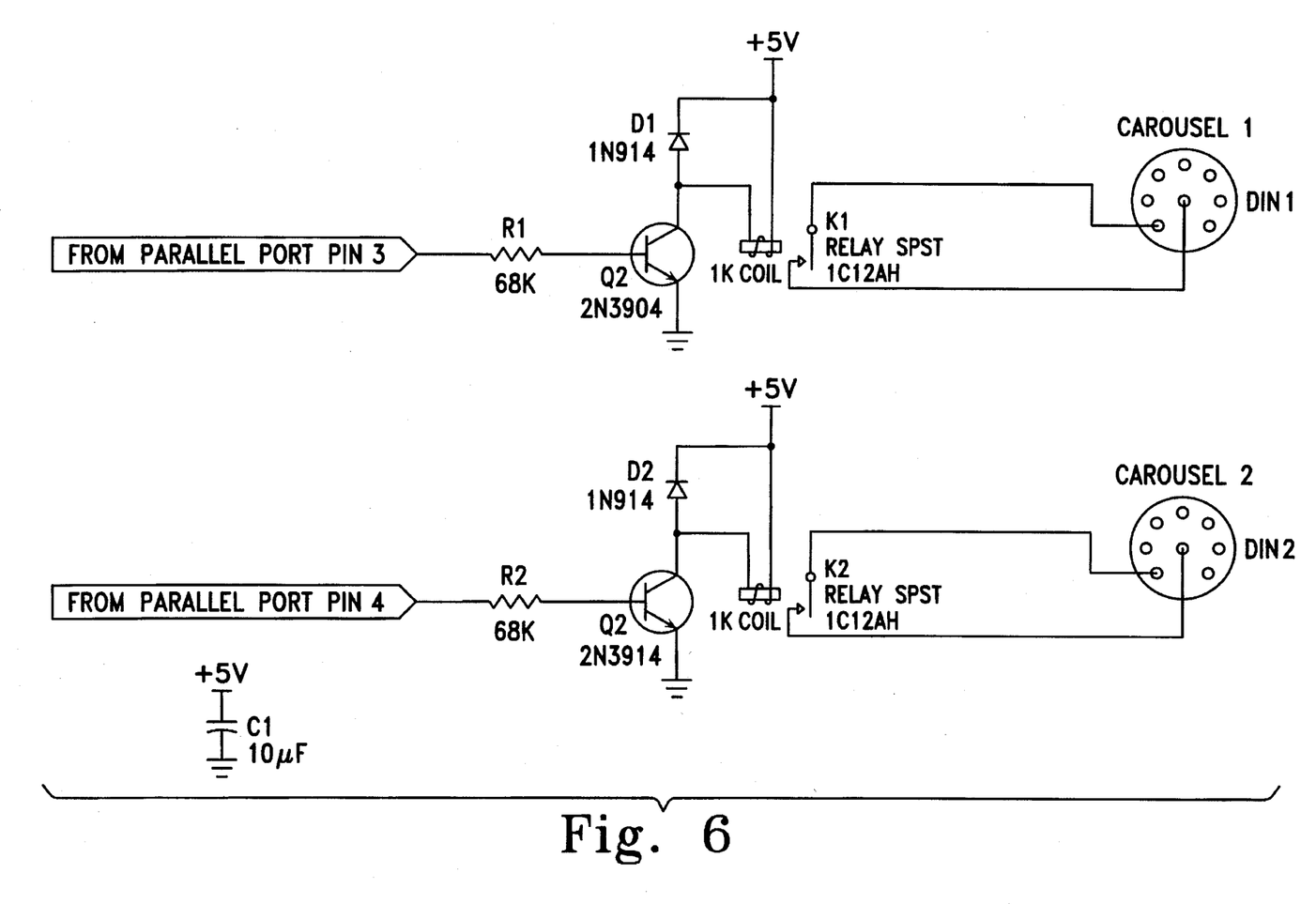
FIG. 6 shows the turntable rotation controller circuitry.

Computer 44 functions are supervisory as well as for data acquisition, storage, data analysis, and presentation. The software, written in Borland C++, controls system operation, manages the acquired data, and provides a user-friendly interface. A main menu provides access to features of software and information about its ability to automatically recover from a power failure. A configuration menu provides user options for the insect monitoring (data acquisition) mode. Acquired data, which include system operating events as well as insect counts, are temporarily stored in memory (high speed RAM) to insure not missing insect counts. Backing up these data to a file on the hard drive takes the acquisition system off-line for a short time (computer hardware dependent), so the user can choose how often it is done. The system can be set to automatically backup the hard drive file to an archive floppy disk drive at the end of data acquisition. Data acquisition automatically ends after a user selected time interval or by manual user control. The retrigger threshold allows the user to specify the minimum time interval between channel pulses, for each sensor head, that will be recorded as separate insect larva or egg counts. This feature protects against multiple counts from a single insect larva or egg that is slow in clearing the infrared beam. The parallel port information tells computer 44 to which port the BICAP 50 hardware is connected and what Interrupt Request Level (IRQ) level to use. BICAP 50 is designed to run on most IBM-type PC (286 or higher) computers and the benchmark test checks a computer for adequate performance parameters. While scheduled backups prevent total loss of insect data in case of a power failure, failure recovery additionally enables BICAP 50 to automatically resume monitoring when power resumes and provides a complete report of the power failure and its effect on the filed data. The number of insects that must fall into a container before it's turntable is rotated to present the next container can be independently set for each turntable. Other set-ups, such as different number of insects per each container on a single turntable, are possible. The turntable rotation is controlled by the action of a relay switch (FIG. 6), and the number and timing of switch openings and closures can be set to accommodate the specifications of the turntable and the container spacing on the turntable.

Figure 7:
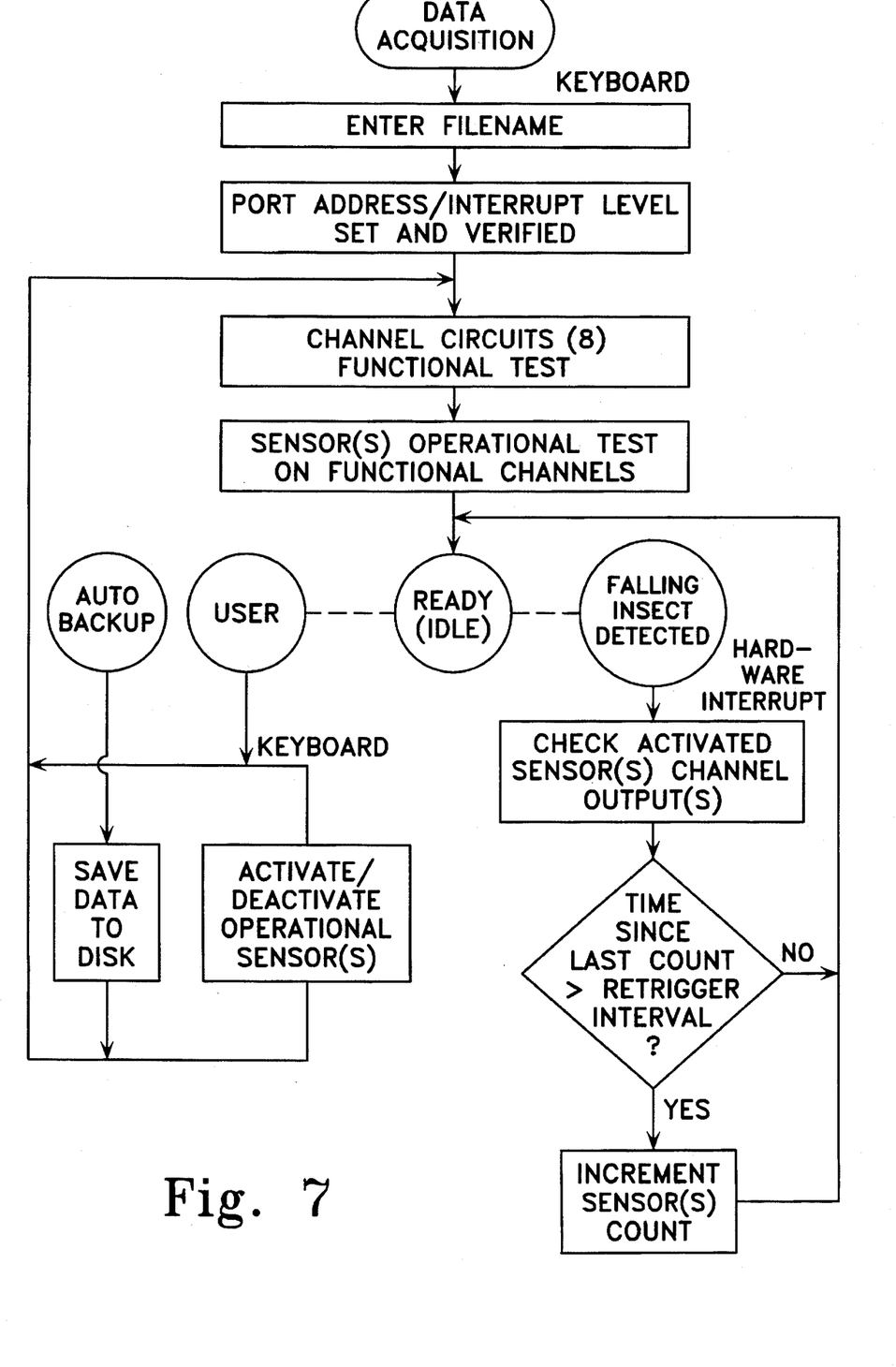
FIG. 7 is a simplified data acquisition flow chart.

A data acquisition screen gives complete sensor head status and usage information, and provides the user with control of the system. A help screen provides comprehensive instructions for operating the system. Upon selecting the acquisition mode, the user is prompted for a data filename and the system initializes and tests itself (FIG. 7). The status result of testing of each channel is either (a) unavailable—channel circuitry not installed, (b) non-operational/idle—channel circuitry installed but sensor head not connected or not working, or (c) operational/idle—ready for use. Monitoring of insects' larva or egg counts for individual operational sensor heads begins when they are activated by the user, which also starts their elapsed active time clock and initiates a system self-check. If such an operational/active probe or channel malfunctions during acquisition (as determined by a system self-check), the status becomes a flashing non-operational/active to alert the user. Since the data acquisition function is interrupt driven, the computer is idle (taking care of clocks, other overhead functions, and potentially available for other chores) until falling larvae or eggs cause an interrupt. The interrupt driven design (as opposed to a polling design) also allows the computer to respond immediately to a falling larva or egg so that a quick succession of counts can be acquired without error. If the interrupt service routine finds a channel pulse and the retrigger interval criterion has been met, then that sensor head's count is incremented and its time since last count clock is reset. The container number that is currently filling and the current count for the container is also displayed. Other system controls initiate a manual system self-check, a data save to the hard drive (which is always accompanied by a system self-check), and a manual termination of the data acquisition function (which is accompanied by a system self-check and a data save to the hard drive). The user is provided with the convenience of separate annotation pages for recording notes about each sensor head during data acquisition, a computer screen blanker which does not interfere with data acquisition, and a troubleshooting display for monitoring several system operational parameters.

The data manager allows the user to view, export to a spreadsheet, or print the acquired data in many formats. These include different data summaries, ordering criteria, and selections of details. The insect larvae or eggs counts recorded for each sensor head are numbered and time-stamped, and the rotations of the turntable are documented. Any counts recorded while the turntable is rotating when insects might fall between containers are noted. This alerts the user that the filled or new container may have more or less insects per container than programmed for, or the correct number of insects. Also, any retriggers caused by less than the minimum time interval between channel pulses are shown.

A computer can be used with one or more digital I/O (DIO) board for applications of 47 or more sensor heads. However, the PC printer parallel port, like a dedicated DIO card, offers digital output lines and interrupt-on-input capability. Software can be used to create a 100 percent compatible PC parallel port with up to 8 bits of digital input. A rudimentary set of C functions allows for reading and writing to the parallel port and installing an interrupt-service routing (ISR) to handle incoming data on the parallel port. Listing One is PPDIO.H; Listing Two is PPDIO.C.

The parallel port is programmed via three separate I/O registers; the input-only data register, the output-only status register, and the input/output control register. The data register, located at the parallel port's base address, takes a standard bit mask that indicates which pins should be sent high and low. Sending information out the parallel port is accomplished with a simple OUT instruction. PPDIO_SendByte() handles this. The parallel port transmits this byte until told to transmit a different one. Note that while the data register can be theoretically read with an IN instruction, the byte read won't be incoming data—it will be the most recent data transmitted. The data register can not be used for input, so both the status and control registers are used. Reading the status register is very straightforward, except that the logic of pin 11 is inverted. The control register is nominally an output-only register, but by taking advantage of the four output lines driven with open-collector drivers, the control register can be forced into giving input. If a high TTL logic level is produced at the control register's corresponding pins, the pins can be driven low via the incoming signals. Thus, by setting the appropriate bits of the control register, the pins can be used as input. This is handled transparently when PPDI0_InstallISR() is called. Reading the control and status registers is accomplished by an IN instruction at the port's base address and relevant offset. The routines PPDIO_ReadStatusRaw() and PPDIO_ReadControlRaw() illustrate how to accomplish this. Because several of the input lines have negative active logic placed upon them by the parallel port, helper functions that translate negative logic would be useful. The routines PPDIO_ReadStatusCooked() and PPDIO_ReadControlCooked() provide this functionality, along with converting reserved and unused bits to 0.

Once input and output are addressed, the communications is made to be interrupt-driven. The parallel port's input lines could be polled; however, this would be cumbersome, time consuming, and error-prone. Interrupt-driven input on the parallel port is achieved by first having the interrupt enable bit set in the control register. Next, an ISR must be installed in the DOS interrupt vector table for the appropriate IRQ. Finally, the port's IRQ must be unmasked from the 8259 Programmable Interrupt Controller's interrupt-enable register. All of this is demonstrated in PPDIO_InstallISR().

AICP 50 uses a simple call-and-acknowledgement method of IRQ determination to solve the problem of detecting which IRQ a given base address or LPT port corresponds to. This involves installing ISRs at IRQs 5 and 7, "calling" the BICAP 50 hardware (which acknowledges the call by generating an interrupt), then seeing which ISR is called. If no ISR is called, either another IRQ is in use or no IRQs are being used for the parallel port. A secondary use of this call-and-response procedure is for hardware testing—if a sensor head is known to be installed and fails to generate a response when requested, then that sensor head must be malfunctioning. Interrupts are generated via pin 10, normally a printer's ACK line. A high-line level sent to pin 10 results in an interrupt being generated, assuming that all other relevant setup has been done.

It has been found that both cable length (from probe to computer) and interrupt latency plays a role in determining whether a signal actually exists at inputs when the ISR is called. With long cable lengths and a fast computer, it was possible for some inputs not to be updated by the time the ISR was executed. Conversely, with a slow computer it was possible for the signal to have come and gone (depending on the length of the generated input) by the time the ISR was called. These timing problems are compensated for in hardware by the interrupt delay control 41 and a long enough channel one shot 39 pulse, respectively.

The following examples illustrate the invention and are not intended to limit the scope of the invention as defined by the claims.

EXAMPLE 1

The leafminer parasitoid, *Opius dissitus*, a wasp, is a larval-pupal parasitoid—it oviposits in leafminer larvae while they are in the leaf. The parasitized larvae emerge and drop off from the leaf to pupate. The adult wasp emerges from the puparium about 12 days after oviposition. Before BICAP 50, parasitized leafminer larvae were collected daily in a cup at the base of a large collection funnel. As production increased, problems became apparent. When more than about 500 larvae drop into a single cup, (a) larvae stick together in clumps causing mortality during adult occlusion, and (b) large numbers of larvae per cup make it difficult to release parasitoids over a wide area. When production reaches 2000–3000 larvae per day, it becomes extremely labor intensive to change the cups frequently when the larvae emerge from the leaves. Furthermore, there has been no efficient way to count the parasitoids being produced or to track the number released in a certain area.

BICAP 50 counts and packages 13,000 parasitoids per week in packages of 200 per package. The number of larvae per cup were hand counted for 10 cups to determine the accuracy of the counter. A mean of 201.2 larvae were found per cup and the standard deviation is ±8.1 larvae. Deviations occur when two larvae stick together and are counted as one or when a larva gets counted more than once when it crawls past the detector rather than falling past it.

The foregoing detailed description is for the purpose of illustration. Such detail is solely for that purpose and those skilled in the art can make variations without departing from the spirit and scope of the invention.

INDEX OF ELEMENTS DESIGNATED BY NUMERAL

24 Sensor head
25 Wall portion
26 Interior chamber
27 Inner top section
28a Funnel-shaped insert
28b Downwardly projecting lip
29 Longitudinally centered inner channel
29b Transparent acetate insert
30 Infrared light-emitting diode (LED)
31 Infrared beam
32 Phototransistor
33 Line
34 Circuitry
35 Shielded cable
36 Buffer
37 AC coupling
38 Threshold detector with hysteresis
39 Channel one-shot
40 Interrupt generator
41 Delay control of interrupt generator
42 Beam generator
43 Computer parallel port
44 Computer
45 Printer parallel port
46 Interrupt line
50 Beneficial insect counting and packaging (BICAP) system
51 Funnel-shaped container
52 Collection cup
53 Turntable
54 Bush lima bean
55 Parasitized leafminer larvae
56 Adjustable sensitivity threshold generator

We claim:

1. A system for counting and packaging insect larvae and eggs comprising
    a counting means for collecting and counting insect larvae, pupae or eggs comprising
        at least one funnel-shaped container and sensor head, wherein said funnel-shaped container sits in the top of said sensor head, and
        at least one turntable means with means for collecting said larvae, pupae or eggs located below each of at least one of said sensor head as they exit said sensor head;
    a detecting means connected to each of said counting means for detecting passage of insect larvae, pupa or egg through said counting means; and
    an analyzing means connected to said detecting means through a means for interfacing wherein said analyzing means receives and analyzes data from said detecting system.

2. The system of claim 1 that includes an interfacing means comprising a channel one-shot, a delay control, and a computer interrupt generator.

3. The system of claim 1 wherein said detecting means comprises
    a plurality of buffers for each of said plurality of counting means,
    a plurality of threshold detectors with hysteresis for each of said plurality of counting means,
    a plurality of channel one-shots for each of said plurality of counting means,
    an interrupt generator for all of said plurality counting means,
    a delay control of interrupt generator for all of said plurality of counting means, and
    a beam generator for all of said plurality of counting means.

4. The system of claim 1 wherein said analyzing means is selected from the group consisting of a computer with one computer parallel port input line interfacing with each of said plurality of counting means through said computer's parallel port and a computer with one digital I/O board input line interfacing with each of said plurality of counting means.

5. The system of claim 1 wherein said turntable means includes a registered advance feature.

6. A method for counting and packaging insect larvae or eggs comprising
    passing insect larvae, pupae or eggs through a means for counting said larvae or eggs,
    detecting the passage of said larvae, pupae or eggs through a sensor head in said counting means using a detecting means attached to said counting means,
    receiving and analyzing data received from said detecting means through a means for interfacing using an analyzing means connected to said detecting means through said interfacing means in order to determine a number of larvae, pupae or eggs passing through the counting means,
    collecting said larvae, pupae or eggs as they pass through said counting means into a container means for packaging said larvae, pupae or eggs, and
    turning a turntable when a predetermined number of larvae, pupae or eggs are in one of said plurality of container means, said turntable being connected to and operated by said analyzing means and said container means being attached to said turntable.

7. The method of 6 wherein said turntable includes a registered advance feature.

* * * * *